(12) United States Patent
Klug et al.

(10) Patent No.: US 10,864,275 B2
(45) Date of Patent: Dec. 15, 2020

(54) N-METHYL-N-ACYLGLUCAMINE-CONTAINING COMPOSITION

(71) Applicant: Clariant International Ltd., Muttenz (CH)

(72) Inventors: Peter Klug, Grossostheim (DE); Carina Mildner, Frankfurt am Main (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/401,354

(22) PCT Filed: May 29, 2013

(86) PCT No.: PCT/EP2013/061065
§ 371 (c)(1),
(2) Date: Nov. 14, 2014

(87) PCT Pub. No.: WO2013/178679
PCT Pub. Date: Dec. 5, 2013

(65) Prior Publication Data
US 2015/0125415 A1 May 7, 2015

(30) Foreign Application Priority Data
May 30, 2012 (DE) .................. 10 2012 010 655

(51) Int. Cl.
| | | |
|---|---|---|
| A61K 47/26 | (2006.01) | |
| A61K 8/34 | (2006.01) | |
| A61K 8/41 | (2006.01) | |
| A61Q 19/00 | (2006.01) | |
| C11D 1/94 | (2006.01) | |
| A61K 8/37 | (2006.01) | |
| A61K 8/42 | (2006.01) | |
| C11D 3/20 | (2006.01) | |
| C11D 3/43 | (2006.01) | |
| A61K 8/04 | (2006.01) | |
| A61K 8/46 | (2006.01) | |
| A61K 8/60 | (2006.01) | |
| A61K 8/86 | (2006.01) | |
| A61K 9/12 | (2006.01) | |
| A61K 47/10 | (2017.01) | |
| A61K 47/20 | (2006.01) | |
| A61Q 5/00 | (2006.01) | |
| A61Q 5/12 | (2006.01) | |
| A61Q 19/10 | (2006.01) | |
| C11D 1/14 | (2006.01) | |
| C11D 1/52 | (2006.01) | |
| C11D 1/90 | (2006.01) | |
| C11D 1/02 | (2006.01) | |

(52) U.S. Cl.
CPC .............. *A61K 47/26* (2013.01); *A61K 8/046* (2013.01); *A61K 8/345* (2013.01); *A61K 8/375* (2013.01); *A61K 8/416* (2013.01); *A61K 8/42* (2013.01); *A61K 8/463* (2013.01); *A61K 8/60* (2013.01); *A61K 8/86* (2013.01); *A61K 9/122* (2013.01); *A61K 47/10* (2013.01); *A61K 47/20* (2013.01); *A61Q 5/00* (2013.01); *A61Q 19/00* (2013.01); *C11D 1/94* (2013.01); *C11D 3/2093* (2013.01); *C11D 3/43* (2013.01); *A61K 2800/592* (2013.01); *A61Q 5/12* (2013.01); *A61Q 19/10* (2013.01); *C11D 1/02* (2013.01); *C11D 1/14* (2013.01); *C11D 1/525* (2013.01); *C11D 1/90* (2013.01)

(58) Field of Classification Search
None
See application file for complete search history.

(56) References Cited

U.S. PATENT DOCUMENTS

| | | |
|---|---|---|
| 2,016,962 A | 10/1935 | Flint |
| 2,667,478 A | 1/1954 | Schwartz |
| 2,703,798 A | 3/1955 | Schwartz |
| 2,891,052 A | 6/1959 | Boettner |
| 2,982,737 A | 5/1961 | Boettner |
| 2,993,887 A | 7/1961 | Zech |
| 4,079,078 A | 3/1978 | Collins |
| 4,400,196 A | 8/1983 | Albrecht |

(Continued)

FOREIGN PATENT DOCUMENTS

| | | |
|---|---|---|
| CA | 2117007 | 9/1994 |
| CA | 1333226 | 11/1994 |

(Continued)

OTHER PUBLICATIONS

The Chemistry of Coconut Oil, accessed online Jul. 12, 2018 (Year: 2018).*
U.S. Appl. No. 14/401,315, now published as US 2015-0133560.
U.S. Appl. No. 14/401,323, now published as US 2015-0141508.
U.S. Appl. No. 14/401,337, now published as US 2015-0141466.
U.S. Appl. No. 14/401,789, now published as US 2015-0126616.
U.S. Appl. No. 14/402,954, now published as US 2015-0140048.
U.S. Appl. No. 14/899,835, now published as US 2016-0143828.
U.S. Appl. No. 14/402,996, now published as US 2015-0164755.
U.S. Appl. No. 14/403,049, now published as US 2015-0150767.
U.S. Appl. No. 14/403,072, now published as US 2015-0164756.
U.S. Appl. No. 14/401,796, now published as US 2015-0126424.

(Continued)

*Primary Examiner* — Melissa S Mercier
(74) *Attorney, Agent, or Firm* — Tod A. Waldrop

(57) ABSTRACT

The invention relates to a composition which contains at least one anionic surfactant, a betaine surfactant, a mixture of N-methyl-N-acylglucamines, the acyl groups of which correspond to those of natural coconut oil and/or palm kernel oil, a glycerol derivative, a solvent and optionally one or more additives. The invention also relates to a method for producing the composition. The invention further relates to the use of the composition for the treatment or care of skin or hair, for example as a shampoo, face cleaner, liquid cleaner or shower gel.

20 Claims, No Drawings

(56) References Cited

U.S. PATENT DOCUMENTS

| | | |
|---|---|---|
| 4,413,087 A | 11/1983 | Bernot |
| 4,481,186 A | 11/1984 | Deckner |
| 4,505,827 A | 3/1985 | Rose |
| 4,565,647 A | 1/1986 | Llenado |
| 4,654,207 A | 3/1987 | Preston |
| 4,681,946 A | 7/1987 | Baur |
| 4,981,684 A | 1/1991 | MacKenzie |
| 5,009,814 A | 4/1991 | Kelkenberg |
| 5,194,639 A | 3/1993 | Connor |
| 5,254,281 A | 10/1993 | Pichardo |
| 5,298,195 A * | 3/1994 | Brumbaugh ......... C11D 3/0094 510/237 |
| 5,317,047 A | 5/1994 | Sabate |
| 5,354,425 A | 10/1994 | Mackey |
| 5,449,770 A | 9/1995 | Shumate |
| 5,454,982 A | 10/1995 | Murch |
| 5,500,155 A | 3/1996 | Weuthen |
| 5,539,134 A | 7/1996 | Strecker |
| 5,559,078 A | 9/1996 | Garst |
| 5,560,873 A | 10/1996 | Chen |
| 5,625,098 A | 4/1997 | Kao |
| 5,691,299 A | 11/1997 | Fabry |
| 5,711,899 A | 1/1998 | Kawa |
| 5,712,235 A | 1/1998 | Nieendick |
| 5,716,922 A | 2/1998 | Curry |
| 5,750,748 A | 5/1998 | Boutique |
| 5,766,267 A | 6/1998 | Schumacher |
| 5,777,165 A | 7/1998 | Kao |
| 5,789,372 A | 8/1998 | Fabry |
| 5,874,096 A | 2/1999 | Hazen |
| 5,945,389 A | 8/1999 | Richard |
| 6,147,045 A | 11/2000 | Lappas |
| 6,147,124 A | 11/2000 | Ansmann |
| 6,165,955 A | 12/2000 | Chen |
| 6,264,961 B1 | 7/2001 | Ansmann |
| 6,274,126 B1 | 8/2001 | Newell |
| 6,288,023 B1 | 9/2001 | Honda |
| 6,329,331 B1 | 12/2001 | Aronson |
| 6,350,788 B1 | 2/2002 | Herold |
| 6,391,962 B2 | 5/2002 | Zerrer |
| 6,455,001 B1 | 9/2002 | Knappe |
| 6,635,708 B1 | 10/2003 | Papenfuhs |
| 6,727,217 B1 | 4/2004 | Nieendick |
| 6,887,838 B2 | 5/2005 | Dykstra |
| 6,903,057 B1 | 6/2005 | Tsaur |
| 7,056,379 B2 | 6/2006 | Nieendick |
| 7,217,752 B2 | 5/2007 | Schmucker-Castner |
| 7,250,392 B1 | 7/2007 | Leonard |
| 7,297,666 B2 | 11/2007 | Kuepper |
| 7,407,667 B2 | 8/2008 | Zerrer |
| 7,578,995 B2 | 8/2009 | Frantz |
| 7,776,318 B2 | 8/2010 | Bissey-Beugras |
| 7,820,771 B2 | 10/2010 | Lapra |
| 7,872,036 B2 | 1/2011 | Toriyabe |
| 7,897,543 B2 | 3/2011 | Bretschneider |
| 8,084,452 B2 | 12/2011 | Jeschke |
| 8,178,481 B2 | 5/2012 | Sans |
| 8,263,538 B2 | 9/2012 | Tsaur |
| 8,324,390 B2 | 12/2012 | Fischer |
| 8,404,855 B2 | 3/2013 | Jeschke |
| 8,536,340 B2 | 9/2013 | Hamamoto |
| 8,637,432 B2 | 1/2014 | Baur |
| 8,729,323 B2 | 5/2014 | Kothandaraman |
| 8,759,255 B2 | 6/2014 | Wacker |
| 8,809,547 B2 | 8/2014 | Bretschneider |
| 8,901,041 B2 | 12/2014 | Frisch |
| 9,187,407 B2 | 11/2015 | Koshti |
| 9,504,636 B2 | 11/2016 | Klug |
| 9,949,909 B2 | 4/2018 | Klug |
| 1,017,277 A1 | 1/2019 | Klug |
| 1,026,525 A1 | 4/2019 | Klug |
| 2001/0023298 A1 | 9/2001 | Weinelt |
| 2001/0056048 A1 | 12/2001 | Bertolosso |
| 2002/0004476 A1 | 1/2002 | Pancheri |
| 2002/0040662 A1 | 4/2002 | Dietz |
| 2002/0065198 A1 | 5/2002 | Highsmith |
| 2002/0168417 A1 | 11/2002 | Blease |
| 2003/0004929 A1 | 1/2003 | Julian |
| 2003/0049292 A1 | 3/2003 | Turowski-Wanke |
| 2003/0069153 A1 | 4/2003 | Jordan |
| 2003/0199403 A1 | 10/2003 | Wells |
| 2004/0086470 A1 | 5/2004 | Nieendick |
| 2005/0037926 A1 | 2/2005 | Zerrer |
| 2005/0037942 A1 | 2/2005 | Otterson |
| 2005/0172859 A1 | 8/2005 | Nieendick |
| 2005/0233935 A1 | 10/2005 | Gunn |
| 2006/0058205 A1 | 3/2006 | Ainger |
| 2006/0079414 A1 | 4/2006 | Nieendick |
| 2006/0089294 A1 | 4/2006 | Depoot |
| 2006/0100127 A1 | 5/2006 | Meier |
| 2006/0110415 A1 | 5/2006 | Gupta |
| 2006/0110432 A1 | 5/2006 | Luu |
| 2006/0135382 A1 | 6/2006 | Molenda |
| 2006/0142291 A1 | 6/2006 | Beilfuss |
| 2006/0166826 A1 | 7/2006 | Zerrer |
| 2006/0171979 A1 | 8/2006 | Calvo |
| 2007/0054820 A1 | 3/2007 | Harichian |
| 2007/0060489 A1 | 3/2007 | Sun |
| 2007/0110700 A1 | 5/2007 | Wells |
| 2007/0128144 A1 | 6/2007 | Bonastre Gilabert |
| 2007/0190004 A1 | 8/2007 | Bockmuhl |
| 2007/0213226 A1 | 9/2007 | Sieverding |
| 2008/0057014 A1 | 3/2008 | Masuda |
| 2008/0317960 A1 | 12/2008 | Pitt |
| 2009/0023622 A1 | 1/2009 | Leidreiter |
| 2009/0111847 A1 | 4/2009 | Li |
| 2009/0118152 A1 | 5/2009 | Lam |
| 2009/0124498 A1 | 5/2009 | Von Deyn |
| 2009/0253612 A1 | 10/2009 | Mushock |
| 2009/0257972 A1 | 10/2009 | Dieker |
| 2010/0051200 A1 | 3/2010 | Mueller |
| 2010/0285077 A1 | 11/2010 | Lintner |
| 2010/0326320 A1 | 12/2010 | Swedo |
| 2011/0002865 A1 | 1/2011 | Fournial |
| 2011/0146536 A1 | 6/2011 | Tomlinson |
| 2011/0150786 A1 | 6/2011 | Desenne |
| 2011/0152150 A1 | 6/2011 | Bernard |
| 2011/0177945 A1 | 7/2011 | Klingelhoefer |
| 2011/0251116 A1 | 10/2011 | Aehle |
| 2011/0263471 A1 | 10/2011 | Barnhart |
| 2012/0009127 A1 | 1/2012 | Dasgupta |
| 2012/0010113 A1 | 1/2012 | Hee |
| 2012/0070388 A1 | 3/2012 | Man |
| 2012/0094890 A1 | 4/2012 | Anantaneni |
| 2012/0172223 A1 | 7/2012 | Wacker |
| 2012/0244092 A1 | 9/2012 | Moser |
| 2013/0030197 A1 | 1/2013 | Harichian |
| 2013/0189212 A1 | 7/2013 | Jawale |
| 2013/0216491 A1 | 8/2013 | Ogihara |
| 2014/0135245 A1 | 5/2014 | Annaheim |
| 2014/0230841 A1 | 8/2014 | Mathonneau |
| 2014/0255330 A1 | 9/2014 | Cron |
| 2014/0303389 A1 | 10/2014 | Crosby |
| 2015/0032003 A1 | 1/2015 | Cho |
| 2015/0125415 A1 | 5/2015 | Klug et al. |
| 2015/0126424 A1 | 5/2015 | Klug et al. |
| 2015/0126616 A1 | 5/2015 | Klug et al. |
| 2015/0133560 A1 | 5/2015 | Klug et al. |
| 2015/0140048 A1 | 5/2015 | Klug et al. |
| 2015/0141466 A1 | 5/2015 | Klug et al. |
| 2015/0141508 A1 | 5/2015 | Klug et al. |
| 2015/0150767 A1 | 6/2015 | Klug et al. |
| 2015/0164755 A1 | 6/2015 | Klug et al. |
| 2015/0164756 A1 | 6/2015 | Klug et al. |
| 2015/0282478 A1 | 10/2015 | Baur |
| 2015/0320037 A1 | 11/2015 | Wacker |
| 2015/0335550 A1 | 11/2015 | Koshti |
| 2016/0074310 A1 | 3/2016 | Klug et al. |
| 2016/0136072 A1 | 5/2016 | Klug et al. |
| 2016/0143828 A1 | 5/2016 | Klug et al. |
| 2016/0243014 A1 | 8/2016 | Dahms et al. |
| 2016/0272666 A1 | 9/2016 | Klug et al. |
| 2016/0361243 A1 | 12/2016 | Klug et al. |
| 2017/0000710 A1 | 1/2017 | Klug et al. |

(56) References Cited

U.S. PATENT DOCUMENTS

| | | |
|---|---|---|
| 2017/0002297 A1 | 1/2017 | Klug et al. |
| 2017/0044434 A1 | 2/2017 | Baur et al. |
| 2017/0055524 A1 | 3/2017 | Baur et al. |
| 2017/0071199 A1 | 3/2017 | Baur et al. |
| 2017/0101606 A1 | 4/2017 | Klug et al. |
| 2017/0218293 A1 | 8/2017 | Klug et al. |
| 2017/0226349 A1 | 8/2017 | Kupfer |
| 2017/0265477 A1 | 9/2017 | Baur et al. |
| 2017/0292062 A1 | 10/2017 | Wylde et al. |
| 2017/0305838 A1 | 10/2017 | Appel et al. |
| 2018/0215879 A1 | 8/2018 | Kupfer |
| 2019/0076344 A1 | 3/2019 | Klug |

FOREIGN PATENT DOCUMENTS

| | | | | |
|---|---|---|---|---|
| CA | 2127644 | 1/1995 | | |
| CN | 1061960 | 6/1992 | | |
| CN | 1077489 | 10/1993 | | |
| CN | 1078746 | 11/1993 | | |
| CN | 1088258 | 6/1994 | | |
| CN | 1140987 | 1/1997 | | |
| CN | 1141653 | 1/1997 | | |
| CN | 1155239 | 7/1997 | | |
| CN | 1292641 | 4/2001 | | |
| CN | 1296524 | 5/2001 | | |
| CN | 1501772 | 6/2004 | | |
| CN | 1518408 | 8/2004 | | |
| CN | 1594518 | 3/2005 | | |
| CN | 100528887 C | 5/2006 | | |
| CN | 1997341 | 7/2007 | | |
| CN | 102186340 | 9/2011 | | |
| CN | 102595882 | 7/2012 | | |
| CN | 103468362 | 12/2013 | | |
| CN | 103468382 | 12/2013 | | |
| CN | 104918490 | 9/2015 | | |
| DE | 1956509 | 5/1971 | | |
| DE | 2226872 A1 | 12/1973 | | |
| DE | 4238211 | 1/1994 | | |
| DE | 4235783 | 4/1994 | | |
| DE | 4435383 | 11/1995 | | |
| DE | 19507531 | 9/1996 | | |
| DE | 19701127 | 7/1998 | | |
| DE | 19808824 | 10/1999 | | |
| DE | 19846429 | 4/2000 | | |
| DE | 19916090 | 10/2000 | | |
| DE | 10117993 | 10/2002 | | |
| DE | 10130357 | 1/2003 | | |
| DE | 102007034438 | 1/2009 | | |
| DE | 202013011412 | 1/2014 | | |
| DE | 202013011413 | 1/2014 | | |
| DE | 102012021647 | 5/2014 | | |
| EP | 0039860 | 11/1981 | | |
| EP | 0048436 | 3/1982 | | |
| EP | 0285768 | 10/1988 | | |
| EP | 0285786 | 10/1988 | | |
| EP | 0336151 | 10/1989 | | |
| EP | 0378985 | 7/1990 | | |
| EP | 0407874 | 1/1991 | | |
| EP | 0539588 | 5/1993 | | |
| EP | 0 550 637 | 7/1993 | | |
| EP | 0572723 | 12/1993 | | |
| EP | 0614881 | 9/1994 | | |
| EP | 0633244 | 1/1995 | | |
| EP | 0709449 | 5/1996 | | |
| EP | 0745719 | 12/1996 | | |
| EP | 0769548 A1 | 4/1997 | | |
| EP | 0774503 A1 | 5/1997 | | |
| EP | 0995994 | 4/2000 | | |
| EP | 1043017 | 10/2000 | | |
| EP | 1 078 978 | 2/2001 | | |
| EP | 1093722 | 4/2001 | | |
| EP | 1110944 | 6/2001 | | |
| EP | 1177223 | 2/2002 | | |
| EP | 1379129 | 1/2004 | | |
| EP | 1422288 | 5/2004 | | |
| EP | 1529832 | 5/2005 | | |
| EP | 1676831 | 7/2006 | | |
| EP | 1716842 | 11/2006 | | |
| JP | S4810053 B | 2/1973 | | |
| JP | S63270534 | 11/1988 | | |
| JP | H06501731 | 2/1994 | | |
| JP | H06501733 | 2/1994 | | |
| JP | H06240599 | 8/1994 | | |
| JP | H07507341 | 8/1995 | | |
| JP | H0812993 | 1/1996 | | |
| JP | H0848618 | 2/1996 | | |
| JP | H09502476 | 3/1997 | | |
| JP | H09506683 | 6/1997 | | |
| JP | H09510956 | 11/1997 | | |
| JP | H10501279 | 2/1998 | | |
| JP | H10508043 | 8/1998 | | |
| JP | H11505839 | 5/1999 | | |
| JP | H11246890 | 9/1999 | | |
| JP | H11512334 | 10/1999 | | |
| JP | 2000512286 | 9/2000 | | |
| JP | 2000297028 | 10/2000 | | |
| JP | 2001501635 | 2/2001 | | |
| JP | 2001131579 | 5/2001 | | |
| JP | 2001247528 | 9/2001 | | |
| JP | 2002542344 A | 12/2002 | | |
| JP | 2006183030 | 7/2006 | | |
| JP | 2006183039 | 7/2006 | | |
| JP | 2007538023 | 12/2007 | | |
| JP | 2008110953 | 5/2008 | | |
| JP | 2010018586 | 1/2010 | | |
| JP | 2010037252 | 2/2010 | | |
| JP | 2013534232 | 9/2013 | | |
| JP | 2014532815 | 12/2014 | | |
| JP | 2015518026 | 6/2015 | | |
| JP | 2017526776 | 9/2017 | | |
| WO | 9205764 A1 | 4/1992 | | |
| WO | 9206073 | 4/1992 | | |
| WO | 9206154 | 4/1992 | | |
| WO | 9206162 A1 | 4/1992 | | |
| WO | WO 92/06158 | 4/1992 | | |
| WO | WO9206161 A | * 4/1992 | | |
| WO | WO 9206161 A1 | * 4/1992 | ............. | C11D 1/525 |
| WO | WO-9206161 A1 | * 4/1992 | ............. | C11D 1/525 |
| WO | 9318125 | 9/1993 | | |
| WO | 9319149 | 9/1993 | | |
| WO | 9410130 | 5/1994 | | |
| WO | 9412608 | 6/1994 | | |
| WO | 9412609 | 6/1994 | | |
| WO | 9419941 | 9/1994 | | |
| WO | 9516824 | 6/1995 | | |
| WO | 9517880 A1 | 7/1995 | | |
| WO | 9519415 | 7/1995 | | |
| WO | 9523840 | 9/1995 | | |
| WO | 9533033 | 12/1995 | | |
| WO | 9533035 | 12/1995 | | |
| WO | WO 9603974 A1 | * 2/1996 | ............... | A61K 8/42 |
| WO | 9610386 | 4/1996 | | |
| WO | 9614374 | 5/1996 | | |
| WO | 9616540 | 6/1996 | | |
| WO | 9628023 | 9/1996 | | |
| WO | 9637589 | 11/1996 | | |
| WO | 9637592 | 11/1996 | | |
| WO | 9747284 A1 | 12/1997 | | |
| WO | 9800496 A1 | 1/1998 | | |
| WO | 9841601 | 9/1998 | | |
| WO | WO 98/56496 | 12/1998 | | |
| WO | 9951716 | 10/1999 | | |
| WO | 0065014 | 11/2000 | | |
| WO | 0137658 | 5/2001 | | |
| WO | 0160877 | 8/2001 | | |
| WO | 02089575 | 11/2002 | | |
| WO | 2002096882 | 12/2002 | | |
| WO | 03000055 | 1/2003 | | |
| WO | 2003106457 | 12/2003 | | |
| WO | 2004056358 | 7/2004 | | |
| WO | 2004099150 | 11/2004 | | |
| WO | 2004099160 | 11/2004 | | |
| WO | 2005035486 | 4/2005 | | |
| WO | 2005063094 | 7/2005 | | |

(56) References Cited

FOREIGN PATENT DOCUMENTS

| | | | |
|---|---|---|---|
| WO | 2005077934 | 8/2005 | |
| WO | 2005117580 | 12/2005 | |
| WO | 2006043635 | 4/2006 | |
| WO | 2006056433 | 6/2006 | |
| WO | 2006089633 | 8/2006 | |
| WO | 2006100288 | 9/2006 | |
| WO | 2007040280 | 4/2007 | |
| WO | 2007057407 | 5/2007 | |
| WO | 2007075459 | 7/2007 | |
| WO | 2007101369 | 9/2007 | |
| WO | 2007115643 | 10/2007 | |
| WO | 2007115644 | 10/2007 | |
| WO | 2007115646 | 10/2007 | |
| WO | 2007147500 | 12/2007 | |
| WO | 2007149134 | 12/2007 | |
| WO | WO-2007141066 A1 * | 12/2007 | ............... C11D 1/74 |
| WO | 2005085216 | 1/2008 | |
| WO | 2008009360 | 1/2008 | |
| WO | 2008066153 | 6/2008 | |
| WO | 2008067911 | 6/2008 | |
| WO | 2008104503 | 9/2008 | |
| WO | 2009002956 | 12/2008 | |
| WO | 2009029561 | 3/2009 | |
| WO | 2009049851 | 4/2009 | |
| WO | 2010005692 | 1/2010 | |
| WO | 2010006713 | 1/2010 | |
| WO | 2010069502 | 6/2010 | |
| WO | 2010074747 | 7/2010 | |
| WO | 2010074751 | 7/2010 | |
| WO | 2010126657 | 11/2010 | |
| WO | 2010138661 | 12/2010 | |
| WO | 2011138450 A2 | 11/2011 | |
| WO | 2012061991 | 5/2012 | |
| WO | 2012116939 | 9/2012 | |
| WO | 2013016270 A1 | 1/2013 | |
| WO | 2013178668 | 12/2013 | |
| WO | 2013178670 A2 | 12/2013 | |
| WO | 2013178671 | 12/2013 | |
| WO | 2013178679 | 12/2013 | |
| WO | 2013178697 | 12/2013 | |
| WO | 2013178700 | 12/2013 | |
| WO | 2013178701 | 12/2013 | |
| WO | 2014056561 A1 | 4/2014 | |
| WO | 2014067663 A1 | 5/2014 | |
| WO | 2014170025 | 10/2014 | |
| WO | 2015082062 | 6/2015 | |
| WO | 2015124302 | 8/2015 | |
| WO | 2016023693 | 2/2016 | |
| WO | 2016041823 | 3/2016 | |

OTHER PUBLICATIONS

U.S. Appl. No. 14/439,052, now published as US 2015-0320037.
U.S. Appl. No. 14/785,599, now published as US 2016-0074310.
U.S. Appl. No. 14/901,090, now published as US 2016-0136072.
U.S. Appl. No. 15/037,172, now published as US 2016-0272666.
U.S. Appl. No. 15/100,165, now published as US 2017-0002297.
U.S. Appl. No. 15/039,970, now published as US 2016-0361243.
U.S. Appl. No. 15/100,039, now published as US 2017-0000710.
U.S. Appl. No. 15/035,120, now published as US 2016-0243014.
U.S. Appl. No. 15/526,464, now published as US 2017-0305838.
U.S. Appl. No. 15/120,097, now published as US 2017-0071199.
U.S. Appl. No. 15/120,103, now published as US 2017-0055524.
U.S. Appl. No. 15/123,065, now published as US 2017-0101606.
U.S. Appl. No. 15/123,143, now published as US 2017-0218293.
U.S. Appl. No. 15/307,205, now published as US 2017-0044434.
U.S. Appl. No. 15/515,324, now published as US 2017-0265477.
U.S. Appl. No. 15/511,987, now published as US 2017-0292062.
U.S. Appl. No. 14/662,564.
U.S. Appl. No. 14/677,500.
U.S. Appl. No. 14/491,615.
U.S. Appl. No. 15/562,852.
U.S. Appl. No. 15/744,645.
English Abstract for DE 4435383, Nov. 9, 1995.
English Abstract for DE 19507531, Sep. 12, 1996.
International Search Report for PCT/EP2013/061100, dated Jul. 16, 2014.
Bezard (Lipids 1971;6:630-634).
Dale et al. (J. Sci. Food. Agric. 1955;6:166-170) (Year: 1955).
English Translation of Cited Excerpts of CN103468382A, Dec. 25, 2013. 2 pages.
Friedrich Vogel: "Kosmetik aus der Sicht des Chemikers", Chemie in Unserer Zeit, No. 5, Jan. 1, 1986, pp. 156-164, XP055109030, DOI: 10.1002/ciuz.19860200504 p. 160.
Hardcopy of http://igf-bingen.de/Croda_produkte.pdf, Dec. 1, 2016. 3 pages.
International Preliminary Report on Patentability for PCT/EP2013/061044, dated Feb. 12, 2014. 7 pages.
International Preliminary Report on Patentability for PCT/EP2014/001723, dated Jun. 8, 2015. 16 pages.
International Preliminary Report on Patentability for PCT/EP2015/000443, dated Jan. 22, 2016. 6 pages.
International Preliminary Report on Patentability for PCT/EP2015/076072, dated May 16, 2017. 5 pages.
International Search Report for PCT/EP2013/061044, dated May 15, 2014. 2 pages.
International Search Report for PCT/EP2013/061047, dated May 22, 2014. 3 pages.
International Search Report for PCT/EP2013/061075, dated May 15, 2014. 2 pages.
International Search Report for PCT/EP2013/061076, mail date May 15, 2014. 2 pages.
International Search Report for PCT/EP2013/061100, dated Jul. 15, 2014. 4 pages.
International Search Report for PCT/EP2014/001723, dated Jan. 5, 2015. 3 pages.
International Search Report for PCT/EP2015/000443, dated Jun. 2, 2015. 2 pages.
International Search Report for PCT/EP2015/000871 dated Jul. 15, 2015. 3 pages.
International Search Report for PCT/EP2015/076072, dated Feb. 29, 2016. 2 pages.
Palm fatty acid distillate (PFAD) [online] retrieved on May 21, 2018 from: https://www.neste.com/ corporate-info/sustainability/sustainable-supply-chain/pfad-residue-palm-oil-refining-process; 1 page. (Year: 2018).
Plante et al. Castor Oil [online] retrieved on 1/13/16 from: http://www.dionex.com/en-us/ webdocs/110518-Po-UHPLC-Castor-Oil-31May2011-LPN2822-01.pdf; 5 pages.
PubChem, Methylmeglumine, 2006. (Year: 2006) 9 pages.
Quack, et al., Fette-Seifen-Anstrichmittel 78, 200(1976). 7 pages.
R. Mohammadi, J. Wassink, a. Amirfazli, "Effect of Surfactants on Wetting of Super-Hydrophobic Surfaces", Langmuir, American Chemical Society, (20041001), vol. 20, No. 22, doi:10.1021/ la049268k, ISSN 07437463, pp. 9657-9662, XP055098502.
Smith, J.T. et al., "Micellar Electrokinetic Capillary Chromatography with in Situ Charged Micelles. 1. Evaluation of N-D-Gluco-N-methylalkanamide Surfactants as Anionic Borate Complexes," Anal. Chem. 1994, 66, 1119-1133.
Söderlind, E. et al., "The usefulness of sugar surfactants as solubilizing agents in parenteral formulations," Elsevier, I nternational !IJournal of Pharmaceutics 252 (2003) pp. 61-71, Aug. 19, 2002.
Study on Synthesis and Properties of "Green" Surfactants—Glucamine derivates, Zhao Handong, Master Thesis, Southern Yangtze University, pp. 5-6, Jul. 25, 2007.
Tan et al. (Appl Microbiol Biotechnol. 47:207-211) (Year: 1997).
Tegeler, T. et al., Special Guest Editor Section: Electrically Driven Microseparation Methods for Pesticides and Metabolites: I. Micellar Electrokinetic Capillary Chromatography of Carbamate Insecticides with Mega-Borate and SDS Surfactants," Journal of AOAC International, vol. 82, No. 6, pp. 1542-1549, Nov. 6, 1999.
V. Bergeron, P. Cooper, C. Fischer. J. Giermanska-Kahn, D. Langevin, and a. Pouchelon, "Polydimethylsiloxane (PDMS)-based antifoams" Colloids and Surfaces A: Physicochemical and Engineering Aspects 122 (1997) 103 120. 18 pages.

(56) References Cited

OTHER PUBLICATIONS

Walter, a. ; Suchy, S.E. ; Vinson, P.K., "Solubility properties of the alkylmethylglucamide surfactants", Biochimica et Biophysica Acta (BBA)-Biomembranes, Elsevier, Amsterdam, NL, Amsterdam, NL, (19901102), vol. 1029, No. 1, doi:10.1016/0005-2736(90)90437-S, ISSN 0005-2736, pp. 67-74, XP023354648.
Zhu, Y-P, et al., "Surface Properties of N-Alkanoyl-N-Methy Glucamines and Related Materials", J. Of Surfactants and Detergents, vol. 2, No. 3, Jul. 1, 1999.6 pages.
Lichtenthaler, F.W., "Carbohydrates as Organic Raw Materials," in Ullmann's Encyclopedia of Industrial Chemistry, Wiley-VCH Verlag, 2010. (34 pages).
"Product Specification: N-octanoyl-N-methylglucamine", Jun. 29, 2000 (Jun. 29, 2000), pp. 1-1, XP055098500, Retrieved from the Internet: Url:http://www.sigmaaldrich.com/Graphics/COfAlnfo/SigmaSAPQM/Spec/03/03129/03129 -BULKSIGMA.pdf.
European Coatings Journal in 2009, vol. 07, pp. 26-28.
International Preliminary Report on Patentability for PCT/EP2016/071750, dated Apr. 10, 2018, 5 pages.
International Search Report for PCT/EP2013/003290, dated Feb. 10, 2014. 5 pages.
International Search Report for PCT/EP2014/001722, dated Jan. 5, 2015. 3 pages.
International Search Report for PCT/EP2015/072453, dated Oct. 23, 2015. 2 pages.
International Search Report for PCT/EP2016/063433, dated Aug. 24, 2016. 2 pages.
International Search Report for PCT/EP2016/071750, dated Jan. 28, 2017, 3 pages.
International Search Report for PCT/EP2016/074085, dated Jan. 3, 2017, 3 pages.
Synergen OS Innovation Spotlight, Sep. 1, 2013, 5 pages.

\* cited by examiner

N-METHYL-N-ACYLGLUCAMINE-CONTAINING COMPOSITION

The invention relates to a composition comprising at least one anionic surfactant, a betaine surfactant, a mixture of N-methyl-N-acylglucamines, a glycerol derivative, a solvent, and optionally one or more additives, and to a method for preparing the composition. The invention relates further to the use of the composition for the treatment or care of the skin or hair, for example as a shampoo, facial cleanser, liquid cleanser or shower gel.

In the preparation of compositions, in particular the preparation of cleansing compositions, a number of criteria are to be observed, such as, for example, a good cleansing action, adequate foaming properties, good skin tolerability, a good feel in relation to the skin, hair and especially no irritation of the mucosa. Skin and hair consist of a plurality of layers which comprise inter alia keratin and collagen as fiber proteins. Anionic surfactants can penetrate the layers and damage them. Ideal cleansing agents for cosmetic or pharmaceutical applications should gently clean the skin or the hair without removing oil from and/or drying the hair and the skin and without causing irritation. Most foaming soaps, shower and bath additives, shampoos and cosmetics fail in this regard or exhibit correspondingly poor foaming behavior.

EP 0 550 637 A1 describes a process for preparing polyhydroxy fatty acid amide materials which can be used inter alia as surfactants. The process is particularly useful when the N-alkylpolyhydroxyamine has the formula $N(R^1)CH_2(CH_2OH)_4CH_2OH$. A $C_{12}$-$C_{20}$-fatty acid methyl ester is preferably used in the process. A preferred process for preparing detergent surfactants is one in which the N-alkylpolyhydroxyamine is an N-methylglucoamine, the fatty acid ester is a $C_{12}$-$C_{20}$-methyl ester or a mixture thereof, the solvent is methanol, and the catalyst is sodium methoxide.

Document WO 92/06158 relates to a low-foam detergent composition comprising at least 1% by weight of a polyhydroxy fatty acid amide surfactant of the formula

wherein $R^1$ is H, $C_1$-$C_4$-hydrocarbon, 2-hydroxyethyl or 2-hydroxypropyl, $R^2$ is $C_5$-$C_{31}$-hydrocarbon, and Z is a polyhydroxy hydrocarbon having a linear hydrocarbon chain with at least three hydroxyl groups bonded directly to the chain, or alkoxylated derivatives thereof; at least 1% of an alkylalkoxylated sulfate surfactant; and optionally a foam-suppressing amount of a foam suppressor which is chosen from monocarboxylic fatty acids and salts thereof, silicone foam suppressors and monostearyl kiakali metal phosphates or phosphate esters, and high molecular weight hydrocarbon foam suppressors and mixtures thereof; wherein the composition has an alkylalkoxylated sulfate:polyhydroxy fatty acid amide weight ratio of from 10:1 to 1:10, preferably from 5:1 to 1:5 and more preferably from 4:1 to 1:1 and the polyhydroxy fatty acid amide comprises less than 4% by weight of a cyclic amide secondary product.

WO 98/56496 relates to a surfactant composition having improved foam stability. The surfactant composition comprises: (a) from approximately 1 to approximately 40% by weight of a sugar-based surfactant; (b) from approximately 1 to approximately 40% by weight of an anionic surfactant; (c) from approximately 0.11 to approximately 10% by weight of an amphoacetate; and (d) remainder water, wherein the amounts by weight are based on the weight of the composition.

Accordingly, the object of the invention is to provide improved compositions, in particular with regard to improved foam behavior.

Surprisingly, it has been found that formulations comprising N-acyl-N-methylglucamines having a chain distribution of natural coconut oil or palm kernel oil are superior in terms of the foam properties to the C12/14 N-acyl-N-methylglucamines mentioned in WO 92/06158. N-Acyl-N-methylglucamines that have been prepared from triglyceride oil and accordingly comprise glycerol and small amounts of glycerol derivatives exhibit particular advantages.

There is accordingly provided a composition comprising:
(A) at least one anionic surfactant as component A,
(B) at least one betaine surfactant as component B selected from the group consisting of an alkyl betaine, an alkylamido betaine and mixtures thereof,
(C) a mixture of N-methyl-N-acylglucamines as component C, wherein the N-methyl-N-acylglucamines have a $C_8$-$C_{22}$-acyl radical and the distribution of the $C_8$-$C_{22}$-acyl radicals corresponds to that of natural coconut oil or palm kernel oil or a mixture of the two,
(D) at least one glycerol derivative as component D, selected from the group consisting of glycerol, monoglycerides, diglycerides, triglycerides, wherein the glycerides in question have at least one $C_8$-$C_{22}$-acyl radical, and mixtures thereof,
(E) at least one solvent as component E, and
(F) optionally one or more additives as component F.

The composition according to the invention is distinguished in particular by a synergistic action of components C and D. As is apparent from the comparative example, a composition without component D does not lead to the same effect as the composition according to the invention. This can be attributed to the fact that the products formed in the reaction of a triglyceride and an N-methylglucamine, in particular in their specific ratio, surprisingly lead to the improved properties.

The anionic surfactant of component A can be, for example, an amino acid surfactant. Preference is given to acyl glycinates, acyl alaninates, acyl aspartates, acyl glutamates and acyl sarcosinates, in particular sodium cocoyl glycinate, potassium cocoyl glycinate, sodium lauroyl glycinate, potassium lauroyl glycinate, sodium cocoyl glutamate, sodium lauroyl glutamate, sodium cocoyl aspartate, sodium lauroyl aspartate and sodium lauroyl sarcosinate.

In a preferred embodiment, component A is selected from one or more compound(s) of formula (I)

wherein $R^1$ represents alkyl, cycloalkyl, aralkyl, aryl, alkoxy, alkoxyalkyl or heterocyclyl and M+ is an alkali metal, alkaline earth metal or substituted or unsubstituted ammonium ion,
and/or of formula (II)

wherein $R^1$ represents alkyl, cycloalkyl, aralkyl, aryl, alkoxy, alkoxyalkyl and heterocyclyl and M+ is an alkali metal, alkaline earth metal or substituted or unsubstituted ammonium ion.

"Alkyl" denotes a saturated aliphatic hydrocarbon group which can be straight-chained or branched and can have from 1 to 20 carbon atoms in the chain. Preferred alkyl groups can be straight-chained or branched and have from 1 to 10 carbon atoms in the chain. Branched means that a lower alkyl group, such as methyl, ethyl or propyl, is attached to a linear alkyl chain. Alkyl is, for example, methyl, ethyl, 1-propyl, 2-propyl, 1-butyl, 2-butyl, 2-methyl-1-propyl (isobutyl), 2-methyl-2-propyl (tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl and 1-octadecyl.

"Cycloalkyl" denotes an aliphatic ring which has from 3 to 10 carbon atoms in the ring. Preferred cycloalkyl groups have from 4 to 7 carbon atoms in the ring.

"Aryl" denotes phenyl or naphthyl.

"Aralkyl" denotes an alkyl group which is substituted by an aryl radical.

"Substituted aralkyl" and "substituted aryl" mean that the aryl group or the alkyl group of the aralkyl group is substituted by one or more substituents selected from alkyl, alkoxy, nitro, carboalkoxy, cyano, halo, alkylmercaptyl, trihaloalkyl or carboxyalkyl.

"Alkoxy" denotes an alkyl-0 group in which "alkyl" has the meaning described above. Lower alkoxy groups are preferred. Examples are methoxy, ethoxy, n-propoxy, iso-propoxy and n-butoxy.

"Lower alkyl" denotes an alkyl group which has from 1 to 7 carbon atoms.

"Alkoxyalkyl" denotes an alkyl group as described above which is substituted by an alkoxy group as described above. Accordingly, the term alkoxyalkyl can be understood as including a polyether.

"Heterocyclyl" denotes a 4- to 10-membered ring structure in which one or more ring atoms are other than carbon, for example N, O or S. Heterocyclyl can be aromatic or non-aromatic, that is to say it can be saturated, partially saturated or completely unsaturated.

Particularly preferred as component A are sodium lauryl sulfate and/or sodium lauryl ether sulfate.

Component B is selected from the group consisting of at least one alkyl betaine, alkylamido betaine or mixtures thereof.

Examples of suitable alkyl betaines are the carboxyalkylation products of secondary and in particular tertiary amines of formula (III)

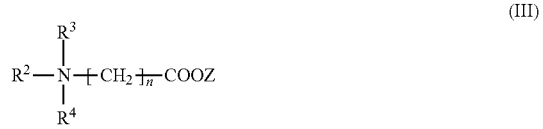

(III)

wherein $R^2$ represents alkyl and/or alkenyl radicals having from 6 to 22 carbon atoms, $R^3$ represents hydrogen or alkyl radicals having from 1 to 4 carbon atoms, $R^4$ represents hydrogen or alkyl radicals having from 1 to 4 carbon atoms, n represents numbers from 1 to 6, and Z represents an alkali and/or alkaline earth metal or ammonium. Typical examples are the carboxymethylation products of hexylmethylamine, hexyldimethylamine, octyldimethylamine, decyldimethylamine, dodecylmethylamine, dodecyl-dimethylamine, dode- cylethylmethylamine, C12/14-coco alkyldimethyl-amine, myristyldimethylamine, cetyldimethylamine, stearyldimethylamine, stearylethylmethylamine, oleyldimethylamine, C16/18-tallow alkyldimethyl-amine and commercial mixtures thereof.

Examples of suitable alkylamido betaines are carboxyalkylation products of amidoamines. Particularly suitable are amidopropyl betaines of formula (IV)

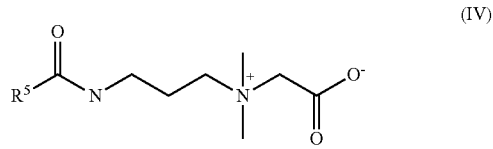

(IV)

wherein $R^5$ is a linear or branched saturated $C_7$-$C_{21}$-alkyl group or a linear or branched mono- or poly-unsaturated $C_7$-$C_{21}$-alkenyl group.

Preferred betaine surfactants are amidopropyl betaines such as cocoamidopropyl betaine ($R^5CO$ is the fatty acid radical of coconut oil, chain length $C_8$-$C_{18}$) and alkyl betaines such as coco-betaine ($R^2$ is the alkyl radical of coconut oil, chain length $C_8$-$C_{18}$) or lauryl betaine ($R^2$ is an alkyl radical of chain length $C_{12}$ and $C_{14}$).

For example and preferably, the N-methyl-N-acylglucamine mixture (C) can be prepared according to EP 0 550 637 from the corresponding triglycerides and N-methylglucamine in the presence of 1,2-propylene glycol as solvent. In a preferred embodiment, components (C) and (D) are formed by transamidation of the triglycerides coconut oil and/or palm kernel oil with N-methylglucamine.

Further terms for N-methyl-N-acylglucamine are N-methyl-N-1-deoxysorbitol fatty acid amide, N-acyl-N-methyl-glucamine, glucamide or N-methyl-N-alkylglucamide. N-Methyl-N-acylglucamine corresponds to formula (V), wherein R is an organic radical:

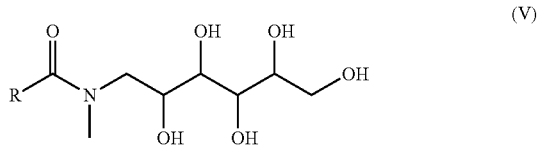

(V)

According to the invention, R—CO corresponds to the $C_8$-$C_{22}$-acyl radicals of natural coconut oil and/or palm kernel oil.

In a preferred embodiment, the distribution of the $C_8$-$C_{22}$-acyl radicals in the N-methyl-N-acylglucamine mixture corresponds to that of natural coconut oil.

The distribution of the $C_8$-$C_{22}$-acyl radicals which corresponds to that of natural coconut oil corresponds to the $C_8$-$C_{22}$-fatty acids in coconut oil.

Coconut oil comprises triglycerides.

Coconut oil comprises
a) from 40 to 55% by weight lauric acid,
b) from 10 to 20% by weight myristic acid,
c) from 8 to 12% by weight palmitic acid,
d) from 6 to 12% by weight oleic acid, and
h) from 0 to 36% by weight further fatty acids,
wherein the sum of the fatty acids bonded to the triglyceride is 100% by weight.

Particularly preferably, coconut oil comprises
a) from 40 to 55% by weight lauric acid,
b) from 10 to 20% by weight myristic acid,
c) from 8 to 12% by weight palmitic acid,
d) from 6 to 12% by weight oleic acid,
e) from 5 to 10% by weight decanoic acid,
f) from 4 to 10% by weight octanoic acid,
g) from 1 to 3% by weight stearic acid, and
h) from 0 to 26% by weight further fatty acids,
wherein the sum of the fatty acids bonded to the triglyceride is 100% by weight.

In a further preferred embodiment, the distribution of the $C_8$-$C_{22}$-acyl radicals in the N-methyl-N-acylglucamine mixture corresponds to that of natural palm kernel oil.

The distribution of the $C_8$-$C_{22}$-acyl radicals which corresponds to that of natural palm kernel oil corresponds to the $C_8$-$C_{22}$-fatty acids in palm kernel oil. Palm kernel oil comprises triglycerides.

Palm kernel oil comprises
a) from 45 to 55% by weight lauric acid,
b) from 14 to 18% by weight myristic acid,
c) from 6 to 10% by weight palmitic acid,
d) from 10 to 17% by weight oleic acid, and
h) from 0 to 25% by weight further fatty acids,
wherein the sum of the fatty acids bonded to the triglyceride is 100% by weight.

Particularly preferably, palm kernel oil comprises
a) from 46 to 49% by weight lauric acid,
b) from 15 to 17% by weight myristic acid,
c) from 7 to 9% by weight palmitic acid,
d) from 13 to 15% by weight oleic acid,
e) from 1 to 3% by weight decanoic acid,
f) from 1 to 3% by weight octanoic acid,
g) from 2 to 4% by weight stearic acid, and
h) from 0 to 15% by weight further fatty acids,
wherein the sum of the fatty acids bonded to the triglyceride is 100% by weight.

In a further preferred embodiment, the distribution of the $C_8$-$C_{22}$-acyl radicals in the N-methyl-N-acylglucamine mixture corresponds to that of a mixture of natural coconut oil and palm kernel oil.

There are used as glycerol derivatives D preferably those formed in the transamidation of coconut oil and/or palm kernel oil with N-methylglucamine. Examples of further glycerol derivatives which come into consideration are triglycerides of linear or branched, saturated or unsaturated, optionally hydroxylated C8-C30-fatty acids, in particular vegetable oils, such as sunflower oil, corn oil, soybean oil, rice oil, jojoba oil, babusscu oil, pumpkin oil, grapeseed oil, sesame oil, walnut oil, apricot oil, orange oil, wheatgerm oil, peach kernel oil, macadamia oil, avocado oil, sweet almond oil, meadow foam seed oil, castor oil, olive oil, groundnut oil, rapeseed oil and coconut oil, as well as synthetic triglyceride oils. Hardened triglycerides are also preferred according to the invention. Oils of animal origin, for example beef tallow, perhydrosqualene and lanolin, can also be used. In addition to the triglycerides, mono- and di-glycerides can also be used.

A solvent E within the scope of the present invention is preferably understood as being protic solvents such as water, $C_1$-$C_8$-alcohols, in particular $C_1$-$C_6$-alcohols, ethylene glycol, diethylene glycol, triethylene glycol or mixtures thereof, particular preference being given to water and/or ethanol or water and/or methanol. Of the $C_1$-$C_6$-alcohols, methanol, ethanol, isopropanol, n-butanol or sec-butanol are preferred.

The preferred solvent is water or mixtures of water and propylene glycol.

Within the scope of a preferred embodiment, the additives F—where present—are chosen from the group consisting of preservatives, fragrances, dyes, surfactants, water, oily substances, cationic polymers, film-forming agents, thickeners and gelling agents, superfatting agents, antimicrobial and biogenic active ingredients, moisture-donating substances, stabilizers, acids, lyes, activity enhancers and mixtures thereof, preferably in amounts of from 0.1 to 10.0% by weight, particularly preferably from 0.5 to 8.0% by weight, and in particular from 1.0 to 5.0% by weight.

Suitable preservatives are the preservatives listed in the relevant annex to the European cosmetic products legislation, for example phenoxyethanol, benzyl alcohol, parabens, benzoic acid and sorbic acid, particularly suitable are, for example, 1,3-bis(hydroxymethyl)-5,5-dimethylimidazolidine-2,4-dione (Nipaguard® DMDMH), piroctone olamine, methylisothiazolinone or mixtures thereof, preferably piroctone, olamine and/or methylisothiazolinone.

As fragrances or perfumes or oils there can be used individual fragrance compounds, for example the synthetic products of the ester, ether, aldehyde, ketone, alcohol and hydrocarbon type. Examples of fragrance compounds of the ester type are benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, linear alkanals having from 8 to 18 carbon atoms, citral, citronellal, citronellyloxy acetaldehyde, cyclamen aldehyde, hydroxycitronellal, lilial and bourgeonal; the ketones include, for example, ionones, alpha-isomethylionone and methyl cedryl ketone; the alcohols include anethol, citronellol, eugenol, geranion, linalool, phenylethyl alcohol and terpineol; the hydrocarbons include mainly terpenes and balsams. Preference is given to the use of mixtures of different fragrances, which together produce a pleasant note.

Perfume oils can also comprise natural fragrance mixtures, as are obtainable from plant or animal sources, for example pine oil, citrus oil, jasmine oil, lily oil, rose oil or ylang-ylang oil. Ethereal oils of low volatility, which are mostly used as flavor components, are also suitable as perfume oils, for example salvia oil, chamomile oil, carnation oil, melissa oil, mint oil, cinnamon leaf oil, linden blossom oil, juniper berry oil, vetiver oil, olibanum oil, galbanum oil and ladanum oil.

The desired viscosity of the compositions can be adjusted (increased or lowered) by adding thickeners and gelling agents. There come into consideration preferably cellulose ethers and other cellulose derivatives (for example carboxymethylcellulose, hydroxyethylcellulose), gelatin, starch and starch derivatives, sodium alginates, fatty acid polyethylene glycol esters, agar-agar, tragacanth or dextrin derivatives, in particular dextrin esters. Also suitable are metal salts of fatty acids, preferably having from 12 to 22 carbon atoms, for example sodium stearate, sodium palmitate, sodium laurate, sodium arachidate, sodium behenate, potassium stearate, potassium palmitate, sodium myristate, aluminum monostearate, hydroxy fatty acids, for example 12-hydroxystearic acid, 16-hydroxyhexadecanoic acid; fatty acid amides; fatty acid alkanolamides; dibenzalsorbitol and alcohol-soluble polyamides and polyacrylamides or mixtures thereof. There can further be used crosslinked and uncrosslinked polyacrylates such as carbomers, sodium polyacrylates or sulfonic-acid-containing polymers such as ammonium acryloyldimethyltaurate/vinylpyrrolidone (VP) copolymer.

There are used as antimicrobial active ingredients, for example, cetyltrimethylammonium chloride, cetylpyridinium chloride, benzethonium chloride, diisobutylethoxyethyldimethylbenzylammonium chloride, sodium N-lauryl sarcosinate, sodium N-palmethyl sarcosinate, lauroyl sarcosine, N-myristoylglycine, potassium N-lauryl sarcosine, trimethylammonium chloride, sodium aluminum chlorohydroxylactate, triethyl citrate, tricetylmethylammonium chloride, 2,4,4'-trichloro-2'-hydroxydiphenyl ether (triclosan), phenoxyethanol, 1,5-pentanediol, 1,6-hexanediol, 3,4,4'-trichlorocarbanilide (triclocarban), diaminoalkylamide, for example L-lysine hexadecylamide, citrate heavy metal salts, salicylates, piroctose, in particular zinc salts, pyrithiones and heavy metal salts thereof, in particular zinc pyrithione, zinc phenolsulfate, farnesol, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, selenium disulfide and octopirox, iodopropynyl butylcarbamate, methylchloroisothiazolinone, methylisothiazolinone, methyldibromo glutaronitrile, AgCl, chloroxylenol, sodium salt of diethylhexyl sulfosuccinate, sodium benzoate, as well as phenoxyethanol, benzyl alcohol, phenoxyisopropanol, parabens, preferably butyl-, ethyl-, methyl- and propyl-paraben, and sodium salts thereof, pentanediol, 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethyloldimethylhydantoin (DMDMH), sodium salt of hydroxymethyl glycinate, hydroxyethylglycine of sorbic acid, and combinations of these active substances.

The compositions according to the invention can further comprise biogenic active ingredients selected from plant extracts, such as, for example, aloe vera, as well as local anesthetics, antibiotics, antiphlogistics, antiallergics, corticosteroids, sebostatic agents, Bisabolol®, Allantoin®, Phytantriol®, proteins, vitamins selected from niacin, biotin, vitamin B2, vitamin B3, vitamin B6, vitamin B3 derivatives (salts, acids, esters, amides, alcohols), vitamin C and vitamin C derivatives (salts, acids, esters, amides, alcohols), preferably as the sodium salt of the monophosphoric acid ester of ascorbic acid or as the magnesium salt of the phosphoric acid ester of ascorbic acid, tocopherol and tocopherol acetate, as well as vitamin E and/or derivatives thereof.

There can be used as stabilizers metal salts of fatty acids, such as, for example, magnesium stearate, aluminum stearate and/or zinc stearate.

There are available as the moisture-donating substance, for example, isopropyl palmitate, glycerol and/or sorbitol.

There can be used as superfatting agents preferably lanolin and lecithin, non-ethoxylated and polyethoxylated or acylated lanolin and lecithin derivatives, polyol fatty acid esters, mono-, di- and tri-glycerides and/or fatty acid alkanolamides, the latter at the same time acting as foam stabilizers, which are preferably used in amounts of from 0.01 to 10% by weight, particularly preferably from 0.1 to 5.0% by weight and most particularly preferably from 0.5 to 3.0% by weight.

As acids or lyes for adjusting the pH there are preferably used mineral acids, in particular HCl, inorganic bases, in particular NaOH or KOH, or organic acids, in particular citric acid.

Within the scope of a preferred embodiment, the composition comprises
(A) from 5 to 15% by weight of component A,
(B) from 1 to 10% by weight of component B,
(C) from 1 to 10% by weight of component C,
(D) from 0.2 to 2.4% by weight of component D,
(E) from 5 to 92.8% by weight of component E, wherein component E is a protic solvent,
(F) from 0 to 10% by weight of component F,
wherein the sum of components A to F is 100% by weight.
Preferably, the composition consists of
(A) from 5 to 15% by weight of component A,
(B) from 1 to 10% by weight of component B,
(C) from 1 to 10% by weight of component C,
(D) from 0.2 to 2.4% by weight of component D,
(E) from 5 to 92.8% by weight of component E, wherein component E is a protic solvent,
(F) from 0 to 10% by weight of component F,
wherein the sum of components A to F is 100% by weight.
Within the scope of a further preferred embodiment, the composition comprises
(A) from 5 to 10% by weight of component A,
(B) from 1 to 7% by weight of component B,
(C) from 1 to 7% by weight of component C,
(D) from 0.2 to 2.4% by weight of component D,
(E) from 5 to 92.8% by weight of component E, wherein component D is a protic solvent,
(F) from 0 to 10% by weight of component F,
wherein the sum of components A to F is 100% by weight.
Within the scope of a particularly preferred embodiment, the composition comprises
(A) from 7 to 10% by weight of component A,
(B) from 1 to 5% by weight of component B,
(C) from 1 to 5% by weight of component C,
(D) from 0.1 to 1.2% by weight of component D,
(E) from 5 to 90.8% by weight of component E, wherein component D is a protic solvent,
(F) from 0.1 to 5% by weight of component F,
wherein the sum of components A to F is 100% by weight.
Within the scope of a preferred embodiment, the sum of components A, B and C is from 7 to 20% by weight, preferably from 10 to 18% by weight and in particular from 10 to 15% by weight.

Preference is given to a ratio of component A:component B:component C of from 2:1:1 to 4:1:1. Particular preference is given to a ratio of 3:1:1.

Within the scope of a preferred embodiment, the composition is a cosmetic, dermatological or pharmaceutical composition.

The invention further provides the use of the composition according to the invention as a shampoo, facial cleanser, liquid cleanser or shower gel.

The invention further provides the use of the composition according to the invention for the treatment or care of the skin.

The invention further provides the use of the composition according to the invention for the treatment or care of the hair.

The invention further provides methods for caring for or treating the skin or hair, wherein the skin or hair is brought into contact with a composition according to the invention.

The invention will be explained in greater detail by the following examples:

Preparation Examples P1 to P3, Example 1 and Comparative Examples 1 to 4.

The N-acyl-N-methyl-glucamines described in the following were prepared according to EP 0 550 637 from the corresponding fatty acid methyl esters or triglycerides and N-methylglucamine in the presence of 1,2-propylene glycol as solvent and were obtained in the form of a solid consisting of active substance and 1,2-propylene glycol. The material obtained in Preparation Examples P1 to P3 comprises the indicated amount of 1,2-propylene glycol and is used directly in the examples shown in Table 2 without being purified further.

TABLE 1

| Preparation Example | Methyl ester | Triglyceride | Active substance (%) | 1,2-Propylene glycol (%) | Melting point (° C.) |
|---|---|---|---|---|---|
| P1 | C12/14 | — | 90 | 10 | 85 |
| P2 | C8/18 (cocoyl) | — | 90 | 10 | 75 |
| P3 | — | C8/18 Coconut oil | 90 | 10 | 50 |

C12/14 means that the methyl ester consists of a mixture of lauric acid methyl ester ($C_{12}$-acyl radical) and myristic acid methyl ester ($C_{14}$-acyl radical) (ratio 75:25). C8/C18 means that the methyl ester consists of a natural distribution of the fatty acids in coconut oil (octanoic acid methyl ester, decanoic acid methyl ester, lauric acid methyl ester and myristic acid methyl ester, palmitic acid methyl ester, stearic acid methyl ester, oleic acid methyl ester, ratio approximately: 4:7:48:20:10:3:8).

Surfactant solutions consisting of sodium lauryl ether sulfate (Genapol LRO liq., Clariant), cocamidopropyl betaine (Genagen CAB 818, Clariant) and sugar-based surfactants were prepared according to Table 2 below and adjusted to a uniform viscosity of 5000 mPas by addition of sodium chloride. The total surfactant content was in each case 12%.

The products were evaluated by a trained sensory panel with 10 participants in respect of the parameters foam quality, foam creaminess, foaming behavior and amount of foam.

In the evaluation: ++=very good, +=good, o=satisfactory, −=adequate, −−=unsatisfactory, the parameters being evaluated qualitatively against the standard (Comparative Example 4) after determination of the mean.

As is clear from the results obtained, the use of N-acyl-N-methylglucamines based on C8/18 triglycerides according to Example 1 (e.g. based on coconut oil) leads, in comparison with a corresponding lauroyl derivative (Comparative Example 1) and a coconut derivative based on methyl ester, to an improved sensory evaluation of the foam behavior of the formulation as compared with the prior art.

The invention claimed is:

1. A composition comprising:
   (A) at least one anionic surfactant as component A,
   (B) at least one betaine surfactant as component B selected from the group consisting of an alkyl betaine, an alkylamido betaine and mixtures thereof,
   (C) a mixture of N-methyl-N-acylglucamines as component C, wherein the N-methyl-N-acylgluamines have a $C_8$-$C_{22}$-acyl radical and wherein the distribution of the $C_8$-$C_{22}$-acyl radicals corresponds to that of $C_8$-$C_{22}$-fatty acids in natural coconut oil, palm kernel oil or a mixture of the two,
   (D) at least one component D selected from the group consisting of monoglycerides, diglycerides, triglycerides, and mixtures thereof, wherein the glycerides in question have at least one $C_8$-$C_{22}$-acyl radical and are formed by the transamidation of coconut oil, palm kernel oil or a mixture of the two with an N-methylglucamine,
   (E) at least one solvent as component E, and
   (F) optionally one or more additives as component F,
   wherein components C and D are prepared by transamidation of triglycerides of coconut oil, palm kernel oil or a mixture of the two with N-methylglucamine.

2. The composition as claimed in claim 1, wherein the distribution of the $C_8$-$C_{22}$-acyl radicals corresponds to that of $C_8$-$C_{22}$-fatty acids in natural coconut oil.

3. The composition as claimed in claim 1, comprising:
   (A) from 5 to 15% by weight of component A,
   (B) from 1 to 10% by weight of component B,
   (C) from 1 to 10% by weight of component C,
   (D) from 0.2 to 2.4% by weight of component D,
   (E) from 5 to 92.8% by weight of component E, wherein component E is a protic solvent, and
   (F) from 0 to 10% by weight of component F,
   wherein the sum of components A to F is 100% by weight.

TABLE 2

| Example | Sugar-based surfactant | Ratio sodium lauryl ether sulfate/cocamido-propyl betaine/sugar-based surfactant | Foam quality | Foam creaminess | Foaming behavior | Amount of foam |
|---|---|---|---|---|---|---|
| Comparative Example 1 | Preparation Example P1 | 6:2:2 | o | o | o | + |
| Comparative Example 2 | Preparation Example P2 | 6:2:2 | + | + | + | + |
| Example 1 | Preparation Example P3 | 6:2:2 | ++ | ++ | ++ | ++ |
| Comparative Example 4 | — | 7:3 | o | o | o | o |

4. The composition as claimed in claim 1, wherein components C and D have been prepared by the reaction of a triglyceride and N-methylglucamine.

5. The composition as claimed in claim 1, wherein component A is selected from the group consisting of one or more compound(s) of formula (I)

$$R^1SO_3^-M^+ \qquad (I)$$

wherein $R^1$ is alkyl, cycloalkyl, aralkyl, aryl, alkoxy, alkoxyalkyl and heterocyclyl and M+ is an alkali metal, alkaline earth metal or substituted or unsubstituted ammonium ion,
and of formula (II)

$$R^1SO_4^-M^+ \qquad (II)$$

wherein $R^1$ is alkyl, cycloalkyl, aralkyl, aryl, alkoxy, alkoxyalkyl and heterocyclyl and M+ is an alkali metal, alkaline earth metal or substituted or unsubstituted ammonium ion.

6. The composition as claimed in claim 1, wherein component E is water or a mixture of water and propylene glycol.

7. The composition as claimed in claim 1, wherein the sum of components A, B and C is from 7 to 35% by weight.

8. The composition as claimed in claim 1, wherein the one or more additives F are selected from the group consisting of preservatives, fragrances, dyes, further surfactants, water, oily substances, cationic polymers, film-forming agents, thickeners and gelling agents, superfatting agents, antimicrobial and biogenic active ingredients, moisture-donating agents, stabilizers, acids, lyes, activity enhancers, and mixtures thereof.

9. The composition as claimed in claim 1, wherein the composition is a cosmetic, dermatological or pharmaceutical composition.

10. A shampoo, facial cleanser, liquid cleanser or shower gel comprising the composition as claimed in claimed 1.

11. A skin treatment or skin care product comprising a composition as claimed in claim 1.

12. A hair treatment or hair care product comprising a composition as claimed in claim 1.

13. A method for caring for or treating the skin, wherein the skin is brought into contact with a composition as claimed in claim 1.

14. A method for caring for or treating the hair, wherein the hair is brought into contact with a composition as claimed in claim 1.

15. The composition as claimed in claim 1, wherein the distribution of the $C_8$-$C_{22}$-acyl radicals of component C corresponds to that of $C_8$-$C_{22}$-fatty acids in natural coconut oil and comprises
   a) from 40 to 55% by weight lauric acid,
   b) from 10 to 20% by weight myristic acid,
   c) from 8 to 12% by weight palmitic acid,
   d) from 6 to 12% by weight oleic acid, and
   h) from 0 to 36% by weight further fatty acids,
wherein the sum of the fatty acids bonded to the triglyceride is 100% by weight.

16. The composition as claimed in claim 1, wherein the distribution of the $C_8$-$C_{22}$-acyl radicals of component C corresponds to that of $C_8$-$C_{22}$-fatty acids in natural coconut oil and comprises
   a) from 40 to 55% by weight lauric acid,
   b) from 10 to 20% by weight myristic acid,
   c) from 8 to 12% by weight palmitic acid,
   d) from 6 to 12% by weight oleic acid,
   e) from 5 to 10% by weight decanoic acid,
   f) from 4 to 10% by weight octanoic acid,
   g) from 1 to 3% by weight stearic acid, and
   h) from 0 to 26% by weight further fatty acids,
wherein the sum of the fatty acids bonded to the triglyceride is 100% by weight.

17. A hair treatment or hair care product comprising a composition comprising:
   (A) at least one anionic surfactant as component A,
   (B) at least one betaine surfactant as component B selected from the group consisting of an alkyl betaine, an alkylamido betaine and mixtures thereof,
   (C) a mixture of N-methyl-N-acylglucamines as component C, wherein the mixture of N-methyl-N-acylglucamines have a $C_8$-$C_{22}$-acyl radical and the distribution of the $C_8$-$C_{22}$-acyl radicals corresponds to that of $C_8$-$C_{22}$-fatty acids in natural coconut oil, palm kernel oil or a mixture of the two,
   (D) at least one component D selected from the group consisting of monoglycerides, diglycerides, triglycerides, wherein the glycerides in question have at least one $C_8$-$C_{22}$-acyl radical, and are formed by the transamidation of coconut oil, palm kernel oil or a mixture of the two with an N-methylglucamine and mixtures thereof,
   (E) at least one solvent as component E, and
   (F) optionally one or more additives as component F,
wherein components C and D are prepared by transamidation of triglycerides of coconut oil, palm kernel oil or a mixture of the two with N-methylglucamine.

18. The composition of claim 1, wherein the distribution of the $C_8$-$C_{22}$-acyl radicals of components C and D are both obtained from $C_8$-$C_{22}$-fatty acids of a natural coconut oil and components C and D are prepared by transamidation of the triglycerides of the natural coconut oil with N-methylglucamine.

19. The composition of claim 1, wherein the distribution of the $C_8$-$C_{22}$-acyl radicals of components C and D are both obtained from $C_8$-$C_{22}$-fatty acids of a natural palm kernel oil and wherein components C and D are prepared by transamidation of the triglycerides of the natural palm kernel oil with N-methylglucamine.

20. The composition of claim 1, wherein the distribution of the $C_8$-$C_{22}$-acyl radicals of components C and D are both obtained from $C_8$-$C_{22}$-fatty acids of a mixture of natural coconut oil and natural palm kernel oil and wherein components C and D are prepared by transamidation of the triglycerides of mixture of the natural coconut oil and that natural palm kernel oil with N-methylglucamine.

* * * * *